US011666767B2

(12) United States Patent
Janzig et al.

(10) Patent No.: US 11,666,767 B2
(45) Date of Patent: Jun. 6, 2023

(54) MEDICAL DEVICE LEAD CONNECTION ASSEMBLY

(71) Applicant: MEDTRONIC, INC., Minneapolis, MN (US)

(72) Inventors: Darren Janzig, Center City, MN (US); Robert J. Davies, Mounds View, MN (US); Seth M. Humphrys, Golden Valley, MN (US); Richard T. Stone, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 492 days.

(21) Appl. No.: 16/091,290

(22) PCT Filed: Apr. 13, 2017

(86) PCT No.: PCT/US2017/027339
§ 371 (c)(1),
(2) Date: Oct. 4, 2018

(87) PCT Pub. No.: WO2017/180827
PCT Pub. Date: Oct. 19, 2017

(65) Prior Publication Data
US 2019/0117982 A1    Apr. 25, 2019

Related U.S. Application Data

(60) Provisional application No. 62/323,080, filed on Apr. 15, 2016.

(51) Int. Cl.
*A61N 1/375* (2006.01)
*B23K 26/21* (2014.01)
(Continued)

(52) U.S. Cl.
CPC ............. *A61N 1/3752* (2013.01); *A61N 1/05* (2013.01); *B23K 15/0046* (2013.01);
(Continued)

(58) Field of Classification Search
CPC ...... A61N 1/05; A61N 1/0551; A61N 1/3605; A61N 1/3752; B23K 15/0046; B23K 2101/36; B23K 26/21
(Continued)

(56) References Cited

U.S. PATENT DOCUMENTS

| 4,769,522 A * | 9/1988 | Lentz ................... B23K 26/262 |
| | | 219/121.63 |
| 6,060,682 A * | 5/2000 | Westbroek ............. B23K 26/24 |
| | | 219/121.64 |

(Continued)

FOREIGN PATENT DOCUMENTS

| EP | 2 281 327 A1 | 2/2011 |
| WO | WO 2009/131725 A1 | 10/2009 |

OTHER PUBLICATIONS

International Preliminary Report on Patentability for PCT/US2017/027339, filed Apr. 13, 2017; dated Oct. 25, 2018, 11 pages.
(Continued)

*Primary Examiner* — Sang Y Paik
(74) *Attorney, Agent, or Firm* — Mueting Raasch Group

(57) ABSTRACT

A method of forming a medical device lead connection element is described. The method includes positioning an end portion of a lead filar to overlap a lead end connection element such that the positioning creates mutual interference between the lead filar and the lead end connection element, and forming an interference configuration. Then melting the
(Continued)

end portion of the lead filar to form a weld joint and allowint the end portion of the lead filar to move towards the end connection element.

18 Claims, 3 Drawing Sheets

(51) Int. Cl.
  *A61N 1/05* (2006.01)
  *B23K 15/00* (2006.01)
  *B23K 101/36* (2006.01)
  *A61N 1/36* (2006.01)

(52) U.S. Cl.
  CPC ............ *B23K 26/21* (2015.10); *A61N 1/0551* (2013.01); *A61N 1/3605* (2013.01); *B23K 2101/36* (2018.08)

(58) Field of Classification Search
  USPC ....... 219/56.1–56.22, 78.01, 85.1, 85.8, 136, 219/137 R
  See application file for complete search history.

(56) References Cited

U.S. PATENT DOCUMENTS

| | | |
|---|---|---|
| 6,477,427 B1 | 11/2002 | Stolz et al. |
| 7,787,961 B1 | 8/2010 | Safarevich et al. |
| 8,525,027 B2 | 9/2013 | Lindner et al. |
| 9,242,089 B2 | 1/2016 | Klardie et al. |
| 2005/0222658 A1 | 10/2005 | Hoegh et al. |
| 2011/0072657 A1 | 3/2011 | Swanson et al. |
| 2011/0106189 A1 | 5/2011 | Seeley et al. |
| 2011/0165785 A1 | 7/2011 | Lindner et al. |
| 2012/0271385 A1* | 10/2012 | Li ........................... C22F 1/183 607/116 |
| 2014/0316502 A1 | 10/2014 | Seeley et al. |

OTHER PUBLICATIONS

International Search Report and Written Opinion for PCT/US2017/027339, filed Apr. 13, 2017; dated Jul. 27, 2017, 11 pages.

\* cited by examiner

MEDICAL DEVICE LEAD CONNECTION ASSEMBLY

This application is the § 371 U.S. National Stage of International Application No. PCT/US2017/027339, filed Apr. 13, 2017, which claims the benefit of U.S. Provisional Application No. 62/323,080, filed Apr. 15, 2016, the disclosures of which are incorporated by reference herein in their entireties.

BACKGROUND

Implantable electrical signal generators, such as pacemakers, defibrillators, neurostimulators, and the like, have been used to treat a variety of diseases. Such devices generate electrical signals that are transferred to a patient's tissue through electrodes present on a distal end portion of a lead. The proximal end portion of a lead, connected to a signal generator, typically contains a number of connectors corresponding to the number of electrodes. Conductors, also referred to as wire filars or filars, run within and along the lead body and electrically couple the connectors to the electrodes.

Fixing the filars that run within the lead body to an end connector is difficult. As the dimensions and size of the implantable medical devices decrease, fixing filars to an end connector becomes even more difficult. Aligning a number of very small filars and joining these filars to the correct connection point on an end connector requires a high level of skill and craftsmanship and takes time to join each filar to each end connector connection point.

SUMMARY

The present disclosure relates to a robust medical device lead connection assembly. The robust connection assembly may efficiently and effectively connect lead filars to connection elements to form implantable leads and extensions.

In one illustrative embodiment, a method includes positioning an end portion of a lead filar to overlap a lead end connection element such that the positioning creates mutual interference between the lead filar and the lead end connection element, and forming an interference configuration. Then melting the end portion of the lead filar to form a weld joint and allow the end portion of the lead filar to move towards the end connection element.

In another illustrative embodiment, a method of forming a medical device lead connection element includes overlapping and contacting an end portion of a lead filar with a connection element to form an overlap portion. Then deflecting the filar overlap portion within an elastic range of the lead filar, to form a loaded state. The method then includes melting the filar overlap region to form a weld pool and allowing the weld pool to cool and form a weld joint.

In another illustrative embodiment, a method of forming a medical device lead connection element includes overlapping and deflecting an end portion of a lead filar with a connection element to form an overlap portion in a loaded configuration. The end portion of a lead filar is deflected within an elastic range of the lead filar. Melting the filar overlap region to form a weld pool and allowing the lead filter end portion to move to a prescribed position and forming a contiguous element with the connection element. The method then includes allowing the weld pool to cool and form a weld joint.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings.

DETAILED DESCRIPTION

Figure 1:
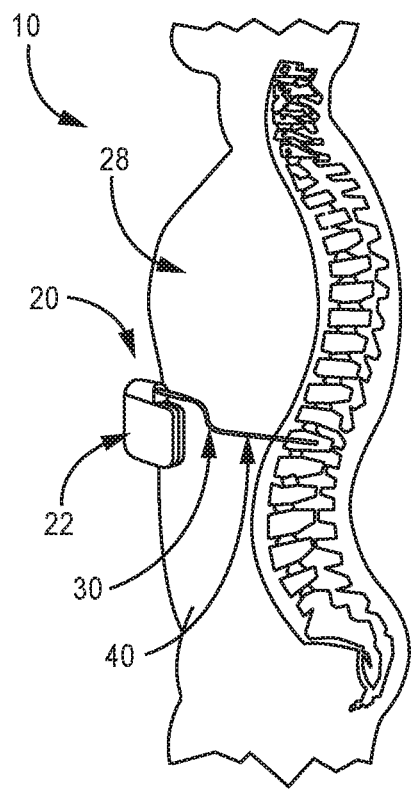
FIG. 1 is a diagrammatic representation of a general environmental view for a neurostimulation system embodiment.

In the following detailed description, reference is made to the accompanying drawings that form a part hereof, and in which are shown by way of illustration several specific embodiments. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The term "coupled" refers to two elements being attached to each other either directly (in direct contact with each other) or indirectly (having one or more elements between and attaching the two elements).

The present disclosure relates to a robust medical device lead connection assembly. The robust connection assembly may efficiently and effectively connect lead filars to connection elements. The robust connection may be formed by contacting a lead filar with another lead filar or connection tab or element. The lead filar and second lead filar or connection tab or element overlap each other and are in flexure. Melting a portion of the lead filar with either the second lead filar or connection tab, relieves the flexural stress and aligns the lead filar with either the second lead filar or connection tab and utilizes surface tension of the weld pool to form a weld joint. This method forms a repeatable, robust weld joint and may be utilized on small diameter filars. While the present disclosure is not so limited, an appreciation of various aspects of the disclosure will be gained through a discussion of the examples provided below.

FIG. 1 shows a general environmental view 10 for an implantable stimulation system. While a stimulation system is illustrated, it is understood that any implantable medical device having a lead body may be utilized with the filar connection and methods described herein.

Stimulation system 20 includes a stimulator 22 (such as a neurostimulator, for example), an optional stimulation lead extension 30, and a stimulation lead 40. Stimulator 22 is typically implanted subcutaneously in a patient's body 28 at a location selected by the clinician; although FIG. 1 illustrates stimulator 22 implanted in the patient's abdomen, other locations are suitable. Stimulation lead 40 is typically fixed in place terminating near the desired location selected by the clinician using a device such as an adjustable anchor.

Figure 2:
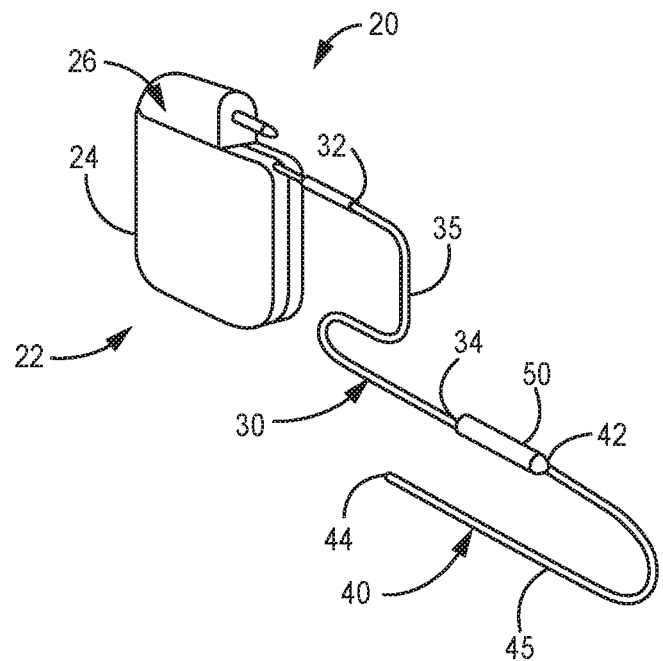
FIG. 2 is a perspective view of the illustrative neurostimulation system of FIG. 1.

FIG. 2 shows an enlarged view of implantable stimulation system 20 having implantable stimulator 22, stimulation lead 40, and optional lead extension 30. Implantable stimulator 22 has a housing 24, a power supply (for example, a battery) within housing 24, and stimulation electronics coupled to the power supply and coupled to a connector block 26, which is also known as a terminal block. Stimulation lead 40 has a lead proximal end 42, a lead distal end 44 and a lead body 45. At lead distal end 44 is an electrode contact having at least one stimulation electrode (not illustrated). Lead extension 30 has an extension proximal end 32, an extension distal end 34, and an extension body 35. Lead proximal end 42 connects to lead extension distal end 34 at connector 50; either or both lead proximal end 42 or extension distal end 34 may include an electrode tip that engages with connector 50.

Lead 40 and lead extension 30 provide electrical communication from stimulator 22 to the electrode contact at distal end 44. Lead distal end 44 contains at least one electrode but in most embodiments has a plurality of such electrodes (for example, 4, 8, 16, etc.). Extending through lead 40 and lead extension 30 are electrically conducting wires, often referred to as filars or wire filars, that couple stimulator 22 to the electrode contact and its electrode(s). The filars may form a multi-filar coil extending along the lead body length.

The lead filars may, for example, be stranded (made up of many small wires), braided-stranded or "BSW" (braided of many small wires), or solid or monofilament. Extending over and covering the wire filars may be an electrically insulating jacket or sheath. Typically, this jacket is a polymeric material, such as ethylene tetrafluoroethylene (ETFE), polytetrafluoroethylene (PTFE), silicone rubber or polyurethane. Other materials that act as electrical insulators can be used. In some embodiments, a shielding layer or jacket may be present, optionally over the insulating jacket. An example of one suitable shielding layer is described in U.S. Patent Application Publication No. 2005/0222658.

This disclosure is directed to a robust connection and methods of welding filars to other filars or connection elements that may form modular components of a lead or lead extension or any component of a lead system. This can be utilized in any number of filar connection points in the lead 40 and/or lead extension 30 to provide electrical communication from stimulator 22 to the electrode contact at a distal end 44 of the lead system. It should be understood that the following discussion of the modular end pieces or interconnects of this invention makes reference to "lead", "leads", "lead body", and the like, generically, and that this discussion is not limiting to positions or uses of the end interconnects of this disclosure, but that they may be used at any location. It should also be understood that the end piece interconnector and the lead structures could be used with applications other than just stimulators.

Figure 3:
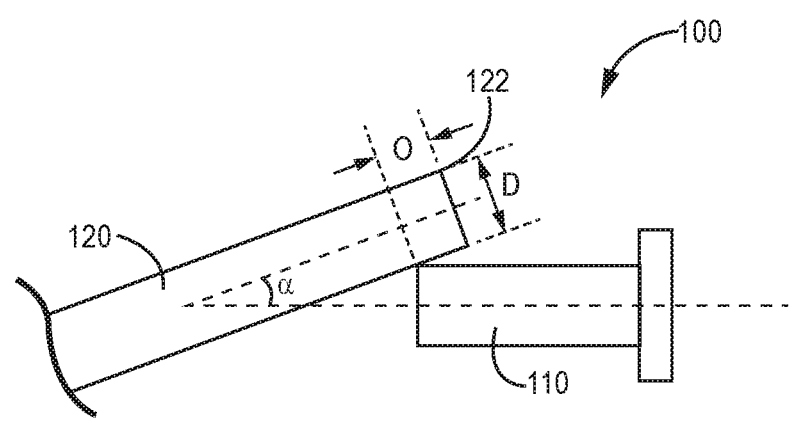
FIG. 3 is schematic diagram of an illustrative filar in flexure with and overlapping a connection element.
Figure 4:
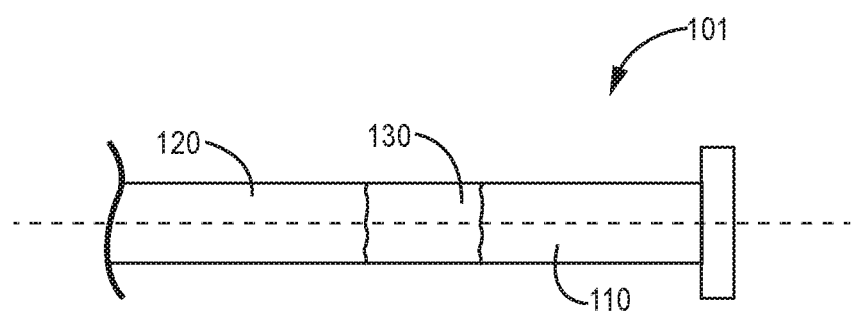
FIG. 4 is a schematic diagram of an illustrative filar aligned with the connection element after melting the lead filar and forming the weld joint.

FIG. 3 is schematic diagram of an illustrative filar 120 in flexure with and overlapping a connection element 110. FIG. 4 is a schematic diagram of an illustrative filar 120 aligned with the connection element 110 after melting the lead filar end portion 122 and forming the weld joint 130.

The lead filar 120 contacts the connection element 110 and the lead filar 120 or the connection element 110 or both flex against each other so that one or both are in flexure, where one or both deflects within the elastic limit of each of the lead filar 120 and the connection element 110. The lead filar 120 may extend the length of the lead body and be in electrical connection with a lead contact at a distal end of the lead body, as described above.

The phrase "elastic limit" refers to the extent to which a solid element may be deflected without permanent alteration to the shape of the solid element. The filar 120 may be elastically deformed or deflected.

One illustrative method of forming a medical device lead connection element includes positioning an end portion 122 of a lead filar 120 to overlap a lead end connection element 110 such that the positioning creates mutual interference (meaning that they both want to occupy the same space) between the lead filar 120 and the lead end connection element 110, and forming an interference configuration. Then melting the end portion 122 of the lead filar 120 to form a weld joint 130 and allow the end portion 122 of the lead filar 120 to move towards the end connection element 110.

One illustrative method of forming a medical device lead connection element includes overlapping and contacting an end portion 122 of a lead filar 120 with a connection element 110 to form an overlap portion "O" having a lateral distance value or length value. The lead filar extends along a length of a lead body and preferably forms a portion of a multi-filar coil as described herein. Then the method includes deflecting the filar overlap portion "O" within an elastic range of the lead filar 120, to form a loaded state. The method then includes melting the filar overlap region "O" to form a weld pool 130 and allowing the weld pool 130 to cool and form a weld joint.

One illustrative embodiment, a method of forming a medical device lead connection element includes overlapping and deflecting an end portion 122 of a lead filar 120 with a connection element 110 to form an overlap portion "O" in a deflected or loaded configuration. The end portion 122 of the lead filar 120 is deflected within an elastic range of the lead filar. Melting the filar overlap region "O" to forms a weld pool 130 and allows the lead filter end portion 122 to move to a prescribed position (or unloaded configuration) and form a contiguous element with the connection element 110. The method then includes allowing the weld pool 130 to cool and form a weld joint.

Melting the filar overlap region "O" to form a weld pool 130 utilizes surface tension of the weld pool to maintain the integrity of the weld pool. Surface tension is surface energy that may define and retain the shape of the weld joint in the molten state. Surface energy or surface tension may overtake a force such as gravity to define and retain the shape of the weld joint in the molten state.

This may be due to the relatively small diameter D of the lead filar 120. It has been found that this connection method is particularly useful when the lead filar 120 has a small diameter. In many of these embodiments the lead filar 120 has a diameter D of less than 250 micrometers, or less than 200 micrometers, or less than 150 micrometers, or less than 125 micrometers, or less than 100 micrometers, or from 50 to 150 micrometers, or from 50 to 125 micrometers, or from 70 to 100 micrometers. The lead filar 120 may be insulated and this insulation may add an additional 5 to 40 micrometers of thickness around the insulated portion of the lead filar 120.

The positioning step may increase static forces at the overlap region resulting in a loaded state and the melting step may decrease these static forces at the overlap, resulting in an unloaded state. The melting step may coalesce the overlap region to form the weld pool. The heating or melting step relieves stress from the lead filar 120 in flexure and/or stress from the connection element 110 in flexure. The heating or melting step causes the lead filar 120 and/or the connection element 110 to move toward each other or align with each other and move away from the flexed or biased position to a relaxed or less-stressed state.

The lead filar 120 may overlap "O" (or extend over the distal end toward the proximal end of) the connection element 110. In many embodiments, the end portion 122 of a lead filar 120 overlaps the connection element 110 by at least a distance value of 0.3(diameter) or 30% of the diameter and by no more than 3 diameters or 300% of the diameter of the lead filar, or in a range from about 0.5 to 2 diameters or in a range from 0.5 to 1 diameter.

In some embodiments, the contacting step forms an angle α between the lead filar 120 and the connection element 110 in a range from 1 to 70 degrees or from 10 to 50 degrees or from 25 to 50 degrees. The melting step reduces the angle α between the lead filar 120 and the connection element 110 by at least 10 degrees, or at least 20 degrees, or at least 30 degrees, or by at least 10%, or at least 25%, or at least 50%.

FIG. 4 is a schematic diagram of an illustrative filar 120 aligned with the connection element 110 after melting the lead filar end portion 122 and forming the weld joint. A weld joint 130 is formed by heating and melting at least a portion of the end portion 122 of a lead filar 120 and a portion of the connection element 110 in contact with the lead filar 120. The weld joint 130 is initially metal in the liquid state. Surface tension holds the liquid metal in the weld pool until it cools to the solid metal weld joint, as described above.

The melting step may form the weld 130 without additional weld material. In many embodiments the weld is formed with a laser weld or an e-beam weld. This is particularly useful when the lead filar 120 and/or the connection element 110 is formed of TiMo or a TiMo alloy. It has been found that β TiMo alloy increases in modulus and strength when heated to the liquid phase (by transforming a portion to an α crystal structure). After the melting step, the weld is cooled to complete the connection.

Figure 5:
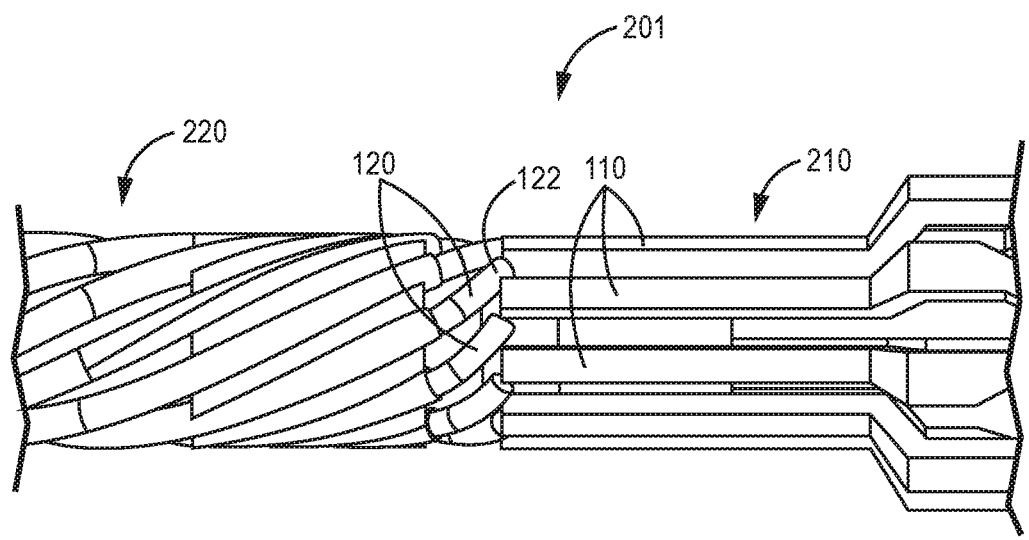
FIG. 5 is a schematic diagram side elevation view of an illustrative medical device lead connection pre-weld.

FIG. 5 is a schematic diagram side elevation view of an illustrative medical device lead connection 201 pre-weld. The medical device lead connection 201 includes a plurality of lead filars 120 in flexure with a corresponding plurality of connection element 110. The connection element 110 forms a portion of the connection element 210 such as connector (described above in FIG. 2). The lead body includes 4 or more, or 8 or more filars 120 in helical or spiral wound along the lead 220 body. In many embodiments, the lead body includes 10 or more, or 12 or more filars 120 in helical or spiral wound along the lead 220 body. Increasing the number of filars in the lead body increases the difficulty in termination of these individual filars to connection elements.

Shielding (not illustrated) may surround the spiral wound filars 120. Once positioned as illustrated, lasers can heat and melt a portion of the lead filar 120 and/or the connection element 110 sequentially or simultaneously to form the connection from the filar to the connection element 210.

The filars 120 in helical or spiral wound along the lead 220 body may form a multi-filar coil having an outer diameter of less than 1.5 millimeters or less than 1 millimeter or in a range from 500 to 900 micrometers or in a range from 625 to 875 micrometers. This multi-filar coil may have an inner diameter in a range from 200 to 1000 micromters or from 350 to 800 micrometers, or from 250 to 600 micrometers. The multi-filar coil inner diameter may define an open lumen that may be configured to receive a stylet for lead placement.

Figure 6:
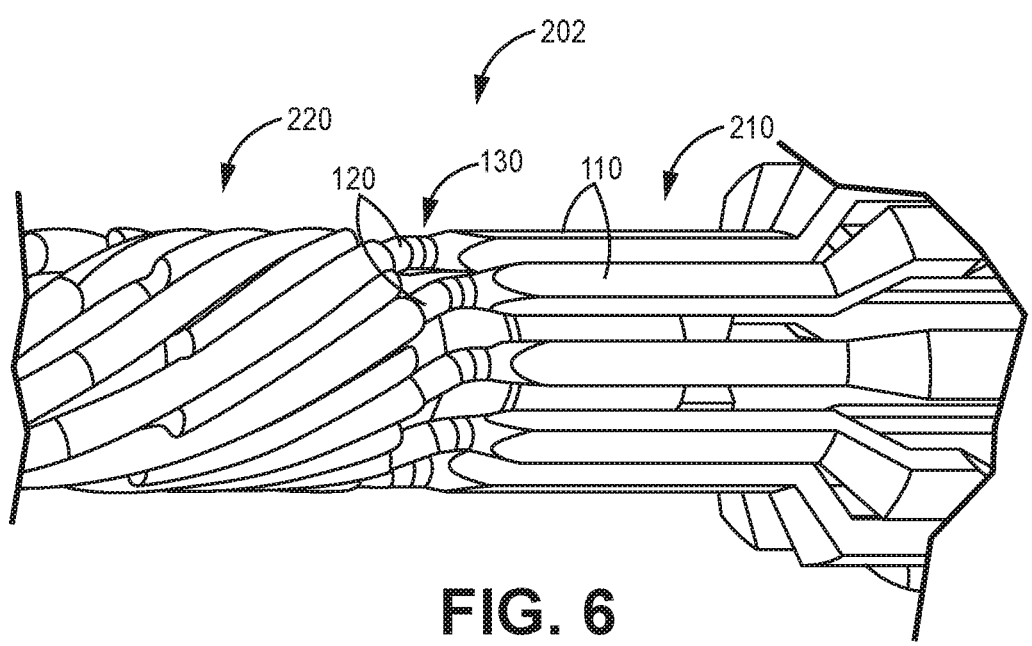
FIG. 6 is a schematic diagram side elevation view of an illustrative medical device lead connection post-weld.

FIG. 6 is a schematic diagram side elevation view of an illustrative medical device lead connection 202 post-weld. The medical device lead connection 202 includes a plurality of lead filars 120 is aligned and fixed to the corresponding plurality of connection elements 110 and forming corresponding weld joints 130. The weld joints 130 may be formed as described above, sequentially or at the same time.

In some embodiments two lead filars 120 (as described above) are in flexure and may be connected as described above. Specifically, contacting a fixed lead filar with an end portion of a second lead filar and heating the lead filars to form a weld joint and release the flexure or stress and allowing the filars to move to a relaxed or aligned state. In embodiments where the lead filars have substantially the same diameter and cross-sectional shape, an isodiametric weld joint is formed.

Thus, embodiments of the MEDICAL DEVICE LEAD CONNECTION ASSEMBLY are disclosed. All references and publications cited herein are expressly incorporated herein by reference in their entirety into this disclosure, except to the extent they may directly contradict this disclosure. Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof. The disclosed embodiments are presented for purposes of illustration and not limitation.

What is claimed is:

1. A method of forming a medical device lead connection element, comprising:
positioning an entire end portion of a lead filar to overlap a lead end connection element such that the positioning elastically deforms the lead end connection element or the end portion of the lead filar and creates mutual interference between the lead filar and the lead end connection element, and forming an interference configuration;
melting the entire end portion of the lead filar to form a weld joint and allow the end portion of the lead filar to move towards the end connection element; and
allowing the weld joint to cool.

2. The method according to claim 1, wherein surface energy defines and retains a shape of the weld joint in the molten state.

3. The method according to claim 1, wherein the positioning step increases static forces at the overlap resulting in a loaded state and the melting step decreases static forces at the overlap resulting in an unloaded state.

4. The method according to claim 1, wherein the melting step coalesces the overlap to form a weld pool.

5. The method according to claim 1, wherein the end portion of the lead filar has a diameter of less than 250 micrometers.

6. The method according to claim 1, wherein the positioning step comprises overlapping the lead end connection element with the end portion of the lead filar by at least a distance value of 0.3(diameter) and no more than 3 diameters of the lead filar.

7. The method according to claim 1, wherein the end portion of the lead filar is formed of TiMo or a TiMo alloy.

8. A method of forming a medical device lead connection element, comprising:
overlapping and contacting an end portion of a lead filar with a connection element to form an overlap portion, the overlap portion comprises an entire end portion of the lead filar that extends past an entire end of the connection element, the lead filar extending along a length of a lead body;
deflecting the lead filar overlap portion within an elastic range of the lead filar, to form a loaded state;
melting the lead filar overlap portion to form a weld pool; and
allowing the weld pool to cool and form a weld joint.

9. The method according to claim 8, wherein the overlapping and contacting step comprises contacting, simultaneously, a plurality of lead end connection elements that extend from a lead connection element with a plurality of end portions of lead filars, wherein selected lead end connection elements each contact a corresponding end portion of a selected lead filar, each lead filar in flexure with and overlapping with the selected lead end connection element.

10. The method according to claim 8, wherein the overlapping and contacting step comprises overlapping and contacting at least 8, forming a multi-filar coil, to a corresponding number of lead end connection elements simultaneously.

11. The method according to claim 8, wherein the overlapping and contacting step forms an angle between the lead end connection element and the overlapping lead filar end portion, and the angle is in a range from 1 to 70 degrees.

12. The method according to claim 8, wherein the melting step relieves stress from the loaded state and forms a less loaded state.

13. The method according to claim 8, wherein the end portion of the lead filar has a diameter of less than 250 micrometers.

14. The method according to claim 8, wherein the overlapping and contacting step comprises overlapping the connection element with the end portion of a lead filar by a distance value of at least 0.3 diameter and no more than 3 diameters of the lead filar.

15. A method of forming a medical device lead connection element, comprising:
overlapping and deflecting an end portion of a lead filar with a connection element to form an overlap portion in a loaded configuration, the end portion of a lead filar being deflected within an elastic range of the lead filar, the overlap portion comprises an entire end portion of the lead filar that extends past an entire end of the connection element;
melting the filar overlap portion to form a weld pool and allowing the lead filar end portion to move to a prescribed position and forming a contiguous element with the connection element; and
allowing the weld pool to cool and form a weld joint.

16. The method according to claim 15, wherein the melting step relieves stress from the loaded configuration and allows the lead filar to move to the prescribed position.

17. The method according to claim 15, wherein the end portion of the lead filar has a diameter of less than 250 micrometers.

18. The method according to claim 15, wherein the overlapping and deflecting step comprises overlapping the connection element with the end portion of a lead filar by at least 0.3 diameter and no more than 3 diameters of the lead filar.

* * * * *